(12) United States Patent
Park et al.

(10) Patent No.: US 11,615,892 B2
(45) Date of Patent: Mar. 28, 2023

(54) METHOD FOR PREDICTING RISK OF DELIRIUM AND DEVICE FOR PREDICTING RISK OF DELIRIUM USING THE SAME

(71) Applicant: INDUSTRY-ACADEMIC COOPERATION FOUNDATION, YONSEI UNIVERSITY, Seoul (KR)

(72) Inventors: Jin Young Park, Seoul (KR); Joo Young Oh, Seoul (KR); Jae Sub Park, Gyeonggi-do (KR); Byeong Soo Lee, Gyeonggi-do (KR); Hak Sik Yang, Seoul (KR)

(73) Assignee: INDUSTRY-ACADEMIC COOPERATION FOUNDATION, YOUNSEI UNIVERSITY, Seoul (KR)

(*) Notice: Subject to any disclaimer, the term of this patent is extended or adjusted under 35 U.S.C. 154(b) by 50 days.

(21) Appl. No.: 16/694,086

(22) Filed: Nov. 25, 2019

(65) Prior Publication Data

US 2020/0168340 A1    May 28, 2020

(30) Foreign Application Priority Data

Nov. 26, 2018 (KR) .......................... 10-2018-147329

(51) Int. Cl.
*G16H 50/30* (2018.01)
*G16H 50/20* (2018.01)
(Continued)

(52) U.S. Cl.
CPC ............. *G16H 50/30* (2018.01); *A61B 5/165* (2013.01); *G06N 3/08* (2013.01); *G16H 20/10* (2018.01); *G16H 50/20* (2018.01)

(58) Field of Classification Search
CPC ........ G16H 50/30; G16H 50/20; G16H 20/10; G16H 50/70; A61B 5/165; A61B 5/4088; A61B 5/7275; G06N 20/00; G06N 3/08
See application file for complete search history.

(56) References Cited

U.S. PATENT DOCUMENTS

2006/0085227 A1*  4/2006  Rosenfeld .............. G16H 40/67
                                                  705/2

FOREIGN PATENT DOCUMENTS

| JP | 2001299702   | * | 10/2001 |
| JP | 2001299702 A |   | 10/2001 |
| KR | 101827793 B1 | * | 2/2018  |

OTHER PUBLICATIONS

"Te-Ming Huang, Kernel Based Algorithms for Mining Huge Data Sets, 2006, Springer, vol. 17" (Year: 2006).*

(Continued)

*Primary Examiner* — Carl H Layno
*Assistant Examiner* — Aya Ziad Bakkar

(57) ABSTRACT

The present disclosure provides a delirium risk predicting method which includes receiving at least one of blood data, severity evaluation data, mental state evaluation data, and bio signal data, medication data, and medical treatment data, for an subject, predicting a delirium risk for the subject, using a delirium risk prediction model configured to predict a delirium risk, based on at least one data, the medication data, and the medical treatment data, and providing the delirium risk predicted for the subject. The at least one data, the medication data, and the medical treatment data are defined as initial data which is evaluated or measured only once for the subject and a delirium risk predicting device using the same.

17 Claims, 11 Drawing Sheets

(51) Int. Cl.
　　　*G06N 3/08*　　　　　(2006.01)
　　　*G16H 20/10*　　　　(2018.01)
　　　*A61B 5/16*　　　　　(2006.01)

(56)　　　　References Cited

OTHER PUBLICATIONS

"Sandeep Grover, Assessment scales for delirium: A review, Aug. 2, 20122, Baishideng" (Year: 2012).*
Office Action for Korean Application No. 10-2018-0147329 dated May 15, 2020; 6 pages.
Office Action for Korean Application No. 10-2018-0147329 dated May 15, 2020; 6 pages; Machine Translation.

* cited by examiner

|  | SUBJECT WITH DELIRIUM | NORMAL SUBJECT | EXCLUDED SAMPLE | ALL |
|---|---|---|---|---|
| LEARNING DATA | 609 | 2656 | 3121 | 6386 |

DEFINITION OF SUBJECT WITH DELIRIUM: SUBJECT DETERMINED TO BE DELIRIUM DURING ENTIRE ICU ADMISSION PERIOD
DEFINITION OF SUBJECT: SUBJECT WHOSE DELIRIUM OCCURRING DATE IS MISSING OR WHO IS DETERMINED NOT TO BE DELIRIUM (ND) AT LEAST ONCE DURING ENTIRE ICU ADMISSION PERIOD

FIG. 3A

| TYPE | FEATURE NAME | FEATURE DESCRIPTION |
|---|---|---|
| MENTAL STATE EVALUATION | RASS | RASS SCORE |
| | STAI | STAI SCORE |
| BIO SIGNAL | PULSE | PULSE RATE |
| | RESP | RESPIRATION RATE |
| | BT | BODY TEMPERATURE |
| | SBP | SBP |
| | DBP | DBP |
| MEDICAL TREATMENT | CATH | WHETHER TO BE CATHETER |
| | FOLEY | WHETHER TO BE FOLEY |
| | VENTIL | WHETHER TO USE MECHANICAL VENTILATOR |
| | RESTR | WHETHER TO USE RESTRAINT |
| | DRAIN | WHETHER TO USE DRAINAGE |
| | NUT | TAKING NUTRITION |
| BLOOD | BUN | BUN-- |
| | PH | ph-- |
| | HCO3 | hco3-- |
| | CRP | crp-- |
| | ALB | alb-- |
| | HB | hb-- |
| | HCT | hct-- |
| | BILI | Bilirubin-- |
| | NA | NA-- |
| SEVERITY EVALUATION | APACHE | APACHE score |
| DRUG | ULTRACET | Ultracet |
| | MIDA | Midazolam |
| | ULTIVA | Ultiva |
| | POFOL | Pofol |
| | ALTIVAN | Altivan |
| | FENTANYL | Fentanyl |
| | PRECEDEX | Precedex |
| | IRCODON | IR codon |
| | TARGIN | TARGIN 20/10 |
| | PERIDOL | Peridol |
| | RISPRDAL | Risperdal |
| | ZYPREXA | Zyprexa |
| | SEROQUEL | Seroquel |
| | ABILIFY | Abilify |
| | PETHIDINE | Pethidine |
| | DUROPAT | durogesic patch |
| | MORPHINE | Morphine |
| | MYPOL | Mypol |

FIG. 3B (a)

| | RAINING | TEST | SUM |
|---|---|---|---|
| D (DELIRIUM) | 487 | 122 | 609 |
| ND (NO DELIRIUM) | 487 | 532 | 1,019 |
| SUM | 974 | 654 | 1,628 |

(b)

| | | OUTPUT RESULT | | |
|---|---|---|---|---|
| | | Positive | Negative | SUM |
| ACTUAL CORRECT ANSWER | Positive | 100 (tp) | 22 (fn) | 122 |
| | Negative | 139 (fp) | 393 (fn) | 532 |
| | SUM | 239 | 415 | 654 |

(c)

| | AUC | Sensitivity (TPR) | Specificity (TNR) | Precision (PPV) | Accuracy |
|---|---|---|---|---|---|
| EVALUATION RESULT | 0.8597 | 0.8197 | 0.7387 | 0.4184 | 0.7538 |

FIG. 4A (a)

|  | RAINING | TEST | SUM |
|---|---|---|---|
| D (DELIRIUM) | 122 | 487 | 609 |
| ND (NO DELIRIUM) | 532 | 487 | 1,019 |
| SUM | 654 | 974 | 1,628 |

(b)

| | | OUTPUT RESULT | | |
|---|---|---|---|---|
| | | Positive | Negative | SUM |
| ACTUAL CORRECT ANSWER | Positive | 101 (tp) | 21 (fn) | 122 |
| | Negative | 133 (fp) | 399(fn) | 532 |
| | SUM | 234 | 420 | 654 |

(c)

|  | AUC | Sensitivity (TPR) | Specificity (TNR) | Precision (PPV) | Accuracy |
|---|---|---|---|---|---|
| EVALUATION RESULT | 0.8585 | 0.8279 | 0.75 | 0.4316 | 0.7645 |

FIG. 4B (a)

| FEATURE | TYPE | FEATURE DESCRIPTION | AVERAGE Relevance |
|---|---|---|---|
| CATH_D2 | MEDICAL TREATMENT | WHETHER TO BE CATHETER (SECOND DAY) | 0.523812 |
| FOLEY_D2 | MEDICAL TREATMENT | WHETHER TO BE FOLEY (SECOND DAY) | 0.44383 |
| RESTR_D2 | MEDICAL TREATMENT | WHETHER TO USE RESTRAINT (SECOND DAY) | 0.258578 |
| RESTR_D1 | MEDICAL TREATMENT | WHETHER TO USE RESTRAINT /9SECOND DAY) | 0.171163 |
| FOLEY_D1 | MEDICAL TREATMENT | WHETHER TO BE FOLEY (FIRST DAY) | 0.167409 |
| VENTIL_D2 | MEDICAL TREATMENT | WHETHER TO USE MECHANICAL VENTILATOR (SECOND DAY) | 0.049444 |
| ULTIVA_D1 | DRUG | Ultiva (FIRST DAY) | 0.030591 |
| ULTRACET_D2 | DRUG | Ultracet ( SECOND DAY) | 0.024423 |
| MORPHINE_D1 | DRUG | Morphine (FIRST DAY) | 0.020187 |
| MYPOL_D2 | DRUG | Mypol (FIRST DAY) | 0.018497 |

(b)

| FEATURE | TYPE | FEATURE DESCRIPTION | AVERAGE Relevance |
|---|---|---|---|
| CATH_D1 | MEDICAL TREATMENT | WHETHER TO BE CATHETER (FIRST DAY) | -0.39132 |
| RASS_D2 | LEVEL | Rass Value (SECOND DAY) | -0.23263 |
| DRAIN_D1 | MEDICAL TREATMENT | WHETHER TO BE DRAINGE (FIRST DAY) | -0.19471 |
| VENTIL_D1 | MEDICAL TREATMENT | WHETHER TO USE MECHANICAL VENTILATOR (FIRST DAY) | -0.10225 |
| PRCEDEX_D2 | DRUG | Precedex (SECOND DAY) | -0.0707 |
| MIDA_D1 | DRUG | Midazolam (FIRST DAY) | -0.0563 |
| MIDA_D2 | DRUG | Midazolam (SECOND DAY) | -0.05462 |
| ULTIVA_D2 | DRUG | Ultiva (SECOND DAY) | -0.05151 |
| BILI_D2 | BLOOD LEVEL | Bilirubin- (SECOND DAY) | -0.0505 |
| APACHE_D1 | SEVERITY EVALUATION | Apache score (FIRST DAY) | -0.05023 |

FIG. 4C

METHOD FOR PREDICTING RISK OF DELIRIUM AND DEVICE FOR PREDICTING RISK OF DELIRIUM USING THE SAME

CROSS-REFERENCE TO RELATED APPLICATIONS

This application claims the priority of Korean Patent Application No. 10-2018-0147329 filed on Nov. 26, 2018, in the Korean Intellectual Property Office, the disclosure of which is incorporated herein by reference.

BACKGROUND

Field

The present disclosure relates to a method and a device for predicting a risk of delirium, and more particularly, to a method configured to predict and provide a risk of delirium based on various clinical data acquired from subjects and a device using the same.

Description of the Related Art

The delirium is a neuropsychiatric disorder characterized by cognitive impairments encompassing disturbances in consciousness and attention, and disorientation and psychotic symptoms such as hallucinations. In this case, the delirium may be divided into three types: a hyperactive type characterized by restless or aggressive behavior, an underactive type characterized by drowsiness, and a mixed type of the above two types.

The delirium may be caused by toxic diseases, metabolic diseases, systemic infections, nervous system infections, brain trauma, or strokes, and be caused due to aftereffects of general anesthesia, major surgery and drug treatment.

For example, substance addictive delirium may be caused by drug treatment such as alcohol, amphetamines, hemp, cocaine, hallucinogens, inhalants, opiates, phencyclidine drugs, sedatives, sleeping pills, and anti-anxiety drugs. The delirium caused in association with the material usage may be caused not only by the addicted state of the material, but also by a lowered concentration of the material in a body fluid when an amount of specific drug is reduced or stopped.

However, it is reported that it is difficult to clinically diagnose the delirium and difficult to treat. More specifically, the delirium may be difficult to be recognized by caregivers or medical practitioners, unlike other diseases. Further, it is difficult to distinguish it from other cognitive impairments such as dementia.

Therefore, for delirium patients, treatment is often delayed and it is difficult to expect good prognosis.

Therefore, there is a continuing need for the development of a new delirium risk prediction system that can predict delirium before it occurs and take a quick action therefor.

The description of the related art has been provided only to facilitate understanding of the present disclosure. The contents in the description of the related art should not be considered as the prior art.

SUMMARY

The inventors of the present disclosure noted that changes in bio signals will be preceded as human body's physiological countermeasures prior to the arrival of a suspicious situation of morbidity of any disease such as delirium.

More specifically, the inventors of the present disclosure noted that for critically ill patients whose condition changes over time, changes in various clinical data available in the intensive care unit may be associated with potential diseases such as delirium.

Specifically, the inventors of the present disclosure noted that the delirium is secondarily caused by other diseases or external environments and recognized that data related to medication or medical treatment prescribed for the patient may be associated with the development of delirium.

As a result, the inventors of the present disclosures recognized that clinical data such as bio signal data, blood data, mental state evaluation and severity evaluation data as well as medication data and medical treatment data could be used to predict the delirium risk for patients, specifically, critically ill patients.

At this time, the inventors of the present disclosure noted initial values of clinical data evaluated or measured initially after patients enter an intensive care unit (or a general ward). More specifically, the inventors of the present disclosure tried to predict delirium for subjects such as patients based on initial data values which are measured or evaluated for the first time in predetermined time units.

As a result, the inventors of the present invention have developed a delirium risk prediction system based on clinical data such as bio signal data, blood data, mental state evaluation and severity evaluation data as well as initial medication data and medical treatment data acquired from the subjects.

In the meantime, the inventors of the present disclosure applied a prediction model trained to predict delirium based on clinical data such as bio signal data, blood data, mental state evaluation and severity evaluation data together with initial medication data and medical treatment data, to a new delirium risk prediction system.

Specifically, the inventors of the present disclosure performed evaluation to determine clinical data having a high relevance to prediction of delirium or clinical data having a high relevance to prediction of a normal state which is not delirium, among various clinical data and try to apply the evaluation result to training of the prediction model. Accordingly, the inventors of the present disclosure expected improvement of diagnostic ability of a prediction model to predict the delirium.

As a result, a new delirium risk prediction system based on a delirium risk prediction model may provide delirium diagnosis information with high accuracy and reliability for subjects.

Furthermore, the inventors of the present disclosure developed the delirium risk prediction system to quickly detect a status of a patient and recognize the delirium risk in advance so that improvement of a treatment outcome of delirium may be expected by advancing a treatment timing of the patient. The inventors of the present disclosure further expected that the development of the delirium risk prediction system may increase a survival rate of the patient, prevent complications, and reduce treatment costs.

Furthermore, the inventors of the present disclosure configured a delirium risk prediction system to provide a feedback which provides information about a delirium inducing drug among received medication data so as to take a quick action for the delirium.

Further, the inventors of the present disclosure configured that when the delirium is predicted from the subject by the prediction model, an alarm is provided to notify the delirium risk so that caregivers or medical practitioners may easily recognize a high risk group of delirium for subjects which are required to be consistently monitored, such as critically ill patients.

Therefore, an object of the present disclosure is to provide a delirium risk predicting method configured to predict a delirium risk for an subject using a delirium risk prediction model configured to predict a delirium risk, based on at least one data of blood data, severity evaluation data, and mental state evaluation data, and bio signal data, medication data, and medical treatment data of the received subject.

Another object of the present disclosure is to provide a delirium risk predicting method configured to determine a delirium inducing drug based on medication data and provide information thereof.

Another object of the present disclosure is to provide a delirium risk predicting device, including a receiver configured to receive at least one of blood data, severity evaluation data, mental state evaluation data, and bio signal data, medication data, and medical treatment data, for an subject and a processor configured to be connected to communicate with the receiver and predict a delirium risk of the subject based on a prediction model.

The objects of the present disclosure are not limited to the aforementioned objects, and other objects, which are not mentioned above, will be apparent to a person having ordinary skill in the art from the following description.

In order to solve the above-described problem, a delirium risk predicting method according to an embodiment of the present disclosure is provided. In this case, the delirium risk predicting method of the present disclosure includes: receiving at least one of blood data, severity evaluation data, mental state evaluation data, and bio signal data, medication data, and medical treatment data, for an subject, predicting a delirium risk for the subject, using a delirium risk prediction model configured to predict a delirium risk, based on at least one data, the medication data, and the medical treatment data, and providing the delirium risk predicted for the subject. In this case, the at least one data, the medication data, and the medical treatment data are defined as initial data which is evaluated or measured only once for the subject.

According to a feature of the present disclosure, the at least one data includes the mental state evaluation data and the mental state evaluation data is a Richmond agitation and sedation scale (RASS) or state-trait anxiety inventory (STAI) score.

According to another feature of the invention, the at least one data includes the blood data and the blood data includes any one value of blood urea nitrogen (BUN), pH, $HCO_3$, albumin (Alb), hemoglobin (Hb), hematocrit (Hct), bilirubin (BILI), Na, and neutrophil to lymphocyte ratio (NLR).

According to yet another feature of the present disclosure, the at least one data includes the severity evaluation data and the severity evaluation data includes acute physiology and chronic health evaluation (APACHE II) score.

According to yet another feature of the present disclosure, the at least one data includes the bio signal data and the bio signal data includes at least one of a pulse rate, a respiration rate, a body temperature, a systolic blood pressure (SBP), and a diastolic blood pressure (DBP).

According to yet another feature of the present disclosure, the medication data includes at least one of Ultracet, Midazolam, ultiva, ativan, pofol, fentanyl, precedex, IR codon, TARGIN 20/10, peridol, risperdal, zyprexa, seroquel, abilify, pethidine, durogesic patch, morphine, and mypol.

According to yet another feature of the present disclosure, the medical treatment data includes at least one medical treatment data of catheter, Foley, mechanical ventilator, restraint, and drainage.

According to yet another feature of the present disclosure, the initial data is defined as initial data which is initially evaluated or measured for the subject in a predetermined time unit for a hospitalization period.

According to yet another feature of the present disclosure, the delirium risk predicting method further comprising: determining a delirium inducing drug based on the medication data, wherein the providing of the delirium risk includes: providing the delirium risk predicted for the subject and the delirium inducing drug.

According to yet another feature of the present disclosure, the providing of the delirium risk includes providing a notification of a delirium risk for the subject when the delirium risk for the subject is predicted by the delirium risk prediction model.

According to yet another feature of the present disclosure, the delirium risk prediction model is a multi-layer perceptron (MLP) algorithm based prediction model.

According to yet another feature of the present disclosure, the delirium risk prediction model is a model trained by receiving learning data configured by at least one of blood data, severity evaluation data, mental state evaluation data, and bio signal data, medication data, and medical treatment data for a delirium sample subject and a normal sample subject; and predicting to be delirium or normal based on the learning data, and the normal sample subject is a subject who clinically does not have delirium and is evaluated not to be delirium.

According to yet another feature of the present disclosure, the delirium risk predicting method further comprising: evaluating the learning data after receiving the learning data, wherein the evaluating of the learning data includes: calculating a relevance score to the delirium for the learning data, and determining delirium related learning data within a predetermined ranking, based on the relevance score.

According to yet another feature of the present disclosure, the evaluating of learning data includes: calculating a relevance score to the delirium for the learning data, using a layer-wise relevance propagation (LRP) algorithm; and determining delirium related learning data within a predetermined ranking, based on the relevance score.

In order to solve the problems as described above, the present disclosure provide a delirium risk predicting device implemented by a processor, the device comprising: a receiver configured to receive at least one of blood data, severity evaluation data, mental state evaluation data, and bio signal data, medication data, and medical treatment data, for a subject; and a processor configured to communicate with the receiver, wherein the processor is configured to predict a delirium risk for the subject, using a delirium risk prediction model configured to predict a delirium risk, based on the at least one data, the medication data, and the medical treatment data and provide the delirium risk predicted for the subject, and the at least one data, the medication data, and the medical treatment data are defined as initial data which is evaluated or measured only once for the subject.

According to feature of the present disclosure, the initial data is defined as initial data which is initially evaluated or measured for the subject in a predetermined time unit for a hospitalization period.

According to another feature of the present disclosure, the processor is further configured to determine a delirium inducing drug based on the medication data and provide the delirium risk predicted for the subject and the delirium inducing drug.

According to yet another feature of the present disclosure, the processor is further configured to provide a notification of a delirium risk for the subject when the delirium risk for the subject is predicted by the delirium risk prediction model.

According to yet another feature of the present disclosure, the medication data includes at least one of Ultracet, Midazolam, ultiva, ativan, pofol, fentanyl, precedex, IR codon, TARGIN 20/10, peridol, risperdal, zyprexa, seroquel, abilify, and pethidine.

According to yet another feature of the present disclosure, the medical treatment data includes at least one medical treatment data of catheter, Foley, mechanical ventilator, restraint, and drainage.

According to the present disclosure, various clinical data is received as well as medication data and medical treatment data for subjects and a delirium risk prediction system based on the received data is provided to quickly detect a delirium risk of subjects and provide relevant information.

Therefore, according to the present disclosure, a good prognosis for a treatment may be provided by advancing a treatment timing for the delirium.

Specifically, the present disclosure can provide a delirium risk prediction system based on clinical data such as bio signal data, blood data, mental state evaluation and severity evaluation data as well as initial medication data and medical treatment data acquired from the subjects, thereby providing early diagnosis of the delirium for the subject.

Therefore, the present disclosure may provide effects such as increased survival rate of the delirium onset subject, prevention of complications, and reduced treatment costs.

Moreover, according to the present disclosure, when a delirium inducing drug is included in the received medication data, a feedback for providing the information is provided so that medical practitioners may take a quick action for the delirium such as discontinuation of administration of delirium inducing drugs.

Further, according to the present disclosure, when the delirium is predicted for the subject by the prediction model, an alarm is provided to notify the delirium risk so that caregivers or medical practitioners may easily recognize a high risk group of delirium for subjects who are required to be consistently monitored, such as critically ill patients.

The effects of the present disclosure are not limited to the aforementioned effects, and various other effects are included in the present specification.

BRIEF DESCRIPTION OF THE DRAWINGS

The above and other aspects, features and other advantages of the present disclosure will be more clearly understood from the following detailed description taken in conjunction with the accompanying drawings, in which:

FIGS. 3A and 3B illustrate learning data of a delirium risk prediction model used for various embodiments of the present disclosure;

FIGS. 4A and 4B illustrate an evaluation result for a delirium risk prediction model used for various embodiments of the present disclosure;

FIG. 4C illustrates clinical data in accordance with a relevance of delirium prediction for a delirium risk prediction model used for various embodiments of the present disclosure.

DETAILED DESCRIPTION OF THE EMBODIMENT

Figure 1A:
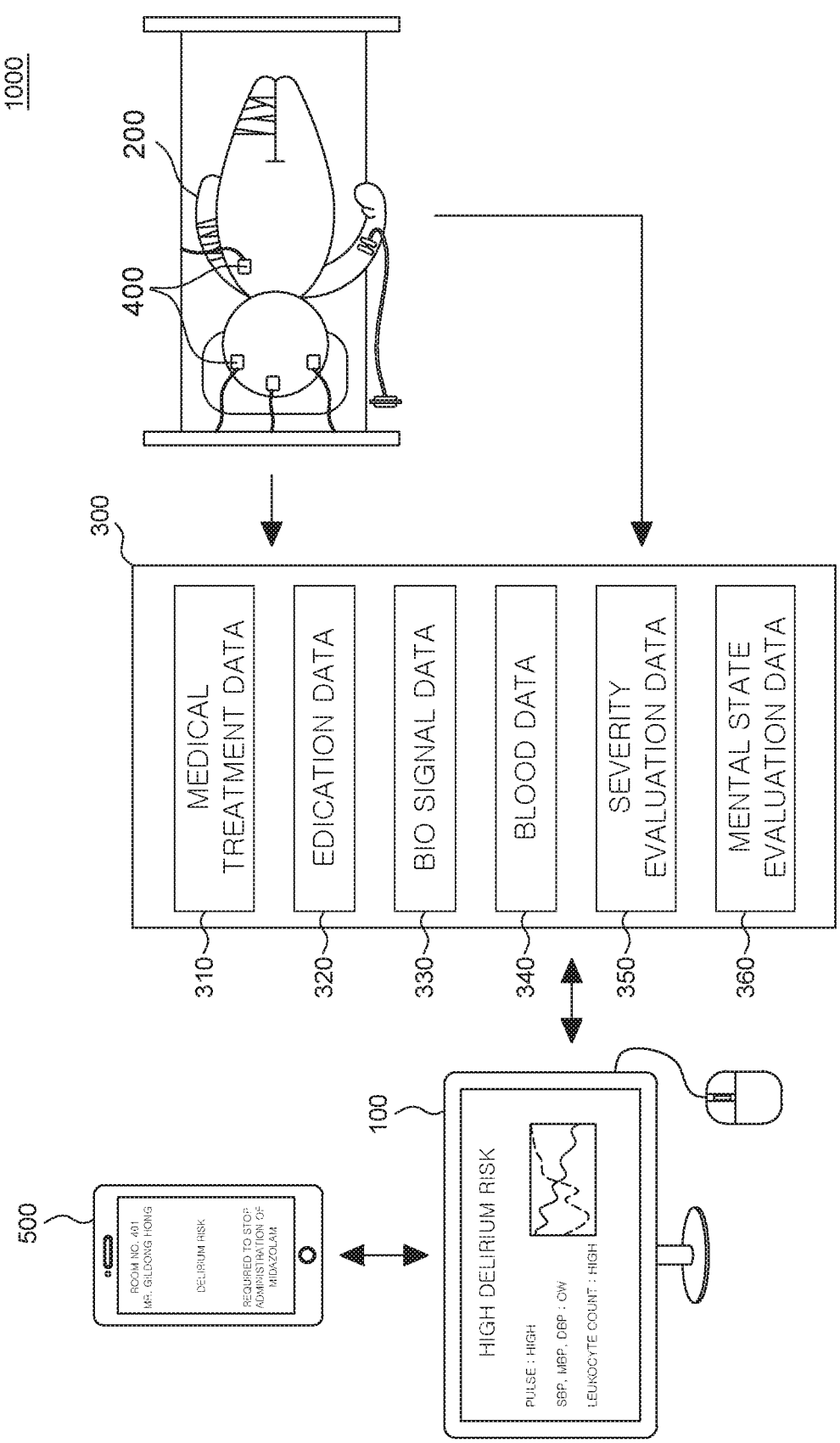
FIG. 1A illustrates a delirium risk prediction system based on a method and a device for predicting a delirium risk according to an embodiment of the present disclosure.

The advantages of the present disclosure and the methods for accomplishment thereof will be apparent from exemplary embodiments described in detail below together with the accompanying drawings. However, the present disclosure is not limited to the following exemplary embodiments but may be implemented in variously different forms. The exemplary embodiments are provided for those skilled in the art to fully understand the present disclosure and the scope of the present disclosure. The present disclosure is defined only by the scope of the appended claims.

A shape, a size, a ratio, an angle, a number, etc. disclosed in the drawings for describing exemplary embodiments of the present disclosure are merely examples, and thus, the present disclosure is not limited to what are illustrated. In the following description, when the detailed description of the relevant known technologies is determined to unnecessarily obscure the gist of the present disclosure, the detailed description thereof will be omitted. The terms such as 'comprise', 'have', and 'include' used herein are generally intended to allow other components to be added unless the terms are used together with the term "only". A component expressed in a singular form includes the component in a plural number unless explicitly stated otherwise.

Components are interpreted to include an error range even if not explicitly stated.

The features of various exemplary embodiments of the present disclosure may be partially or entirely coupled to or combined with each other. As fully understood by those skilled in the art, such features may be technically linked or operated together in various ways, and the exemplary embodiments may be implemented independently of or in association with each other.

For clarification in interpreting the present specification, the terms used herein will be defined below.

A term used in the present specification, "subject" may refer to a target from which a delirium risk is predicted. In the meantime, in the present specification, the subject may refer to a "patient" or a "critically ill patient", but is not limited thereto and may include all targets from which the delirium risk is predicted.

A term used in the present disclosure, "blood data" may refer to clinical data for a biological sample of blood separated from the subject.

For example, the blood data disclosed in this specification may be at least one value of blood urea nitrogen (BUN), pH, HCO$_3$, albumin (Alb), hemoglobin (Hb), hematocrit (Hct), bilirubin (BILI), Na, and neutrophil to lymphocyte ratio (NLR) measured from the blood separated from the subject.

Desirably, the blood data may be initial data initially measured from the subject. For example, when the subject enters an intensive care unit, the blood data may refer to initial blood data initially measured after entering the intensive care unit. Moreover, when the blood data is measured multiple times (for example, three times per day) for the subject in a predetermined time unit (for example, 24 hours), the blood data may include a plurality of blood data acquired for the first time at every predetermined time unit. However, the blood data is not limited thereto.

The term used in this specification, "severity evaluation data" may refer to a value of a scale for evaluating a severity status for a subject.

For example, "severity evaluation data" disclosed in the present specification may be an acute physiology and chronic health evaluation (APACHE II) score.

In this case, the severity evaluation data indicating a severity status of the subject may be relevant to occurrence of the delirium of the subject.

In the meantime, the severity evaluation data may be initial data initially evaluated from the subject. For example, when the subject enters an intensive care unit, the severity evaluation data may refer to initial severity evaluation data initially evaluated after entering the intensive care unit. Moreover, when the severity evaluation is performed multiple times (for example, three times per day) for the subject in a predetermined time unit (for example, 24 hours), the severity evaluation data may refer to initial data acquired for the first time at every predetermined time unit.

The term used in this specification, "mental state evaluation data" may refer to a value of a scale for evaluating a mental state such as anxiety or depression of a subject.

For example, the mental state evaluation data disclosed in the present specification may be Richmond agitation and sedation scale (RASS) or state-trait anxiety inventory (STAI) score. The mental state evaluation data may be relevant to occurrence of delirium.

In the meantime, the mental state evaluation data may be initial data initially evaluated from the subject. For example, when the subject enters an intensive care unit, the mental state evaluation data may refer to initial mental state evaluation data initially evaluated after entering the intensive care unit. Moreover, when the mental state evaluation is performed multiple times (for example, three times per day) for the subject in a predetermined time unit (for example, 24 hours), the mental state evaluation data may include initial data acquired for the first time at every predetermined time unit. However, the mental state evaluation data is not limited thereto.

The term used in the present specification, "bio signal data" refers to data relevant to a condition of the subject such as a vital sign. The bio signal data may be relevant to the delirium risk of the subject.

In this case, the bio signal data may be a body temperature, a pulse rate, an oxygen saturation, a systolic blood pressure, a diastolic blood pressure, a mean blood pressure, and a respiratory rate for the subject measured from the bio signal metrology equipment. However, the bio signal data is not limited thereto and includes various measurement data relevant to the health condition of the subject.

Desirably, the bio signal data may be initial data initially measured from the subject. For example, when the subject enters an intensive care unit, the bio signal data may refer to initial data measured for the first time after entering the intensive care unit. Moreover, when the bio signal data is received multiple times (for example, three times per day) for the subject in a predetermined time unit (for example, 24 hours), the bio signal data may include a plurality of data acquired for the first time at every predetermined time unit.

The term used in the present specification, "medication data" may refer to data relevant to a type of drug administered to the subject and a dose thereof. In the meantime, the drug addiction may cause the delirium so that the medication data may be relevant to the delirium risk of the subject. Therefore, it is important to diagnose and treat the delirium by providing information about the drug having a high relevance to the delirium.

In the meantime, the medication data disclosed in the present specification may include data about administration of at least one of Ultracet, Midazolam, ultiva, ativan, pofol, fentanyl, precedex, IR codon, TARGIN 20/10, peridol, risperdal, zyprexa, seroquel, abilify, and pethidine and a dose thereof. However, the medication data is not limited thereto and includes data about all drugs administered to the subject.

In this case, the medication data may be initial data initially measured from the subject. For example, when the subject enters an intensive care unit, the medication data may refer to initial medication data initially acquired after entering the intensive care unit. Moreover, the medication data may refer to data of initially administered drug, but, it is not limited thereto. For example, when the medication data is received multiple times (for example, three times per day) for the subject in a predetermined time unit (for example, 24 hours), the medication data may include data acquired for the first time at every predetermined time unit.

The term used in the present specification, "medical treatment data" may refer to data indicating whether to perform a medical treatment used for the subject.

For example, the medical treatment data may be data indicating whether to perform at least one medical treatment of catheter, Foley, mechanical ventilator, restraint, and drainage, but, it is not limited thereto.

In the meantime, the medical treatment data may be initial medical treatment data initially measured from the subject. For example, when the subject enters an intensive care unit, the medical treatment data may refer to initial medical treatment data acquired for the first time after entering the intensive care unit. That is, the medical treatment data may refer to all medical treatment data acquired at an initial stage defined as an arbitrary timing. Moreover, the medical treatment data may be data for a medical treatment for the first time used for the subject, but, it is not limited thereto.

For example, when the medical treatment data is acquired multiple times (for example, three times per day) for the subject in a predetermined time unit (for example, hours), the medical treatment data may include data acquired for the first time at every predetermined time unit.

A term used in the present disclosure, "initial data" may refer to clinical data initially evaluated or initially measured for the subject. Moreover, the initial data may refer to all clinical data acquired only once at an arbitrary timing. For example, clinical data of the blood data, the severity evaluation data, the mental state evaluation data, the bio signal data, the medication data, and the medical treatment data disclosed in the present specification may refer to initial data acquired once a day for an subject which enters the ICU after entering the ICU.

Moreover, when a plurality of data is acquired for one day, the clinical data may refer to first acquired data.

The term used in the present specification, a "delirium risk prediction model" may be a model trained to predict the risk of the delirium based on the clinical data such as at least one of initial blood data, severity evaluation data, mental state evaluation data, and bio signal data, medication data and the medical treatment data.

For example, the delirium risk prediction model may be a model trained to predict the delirium risk based on initial clinical data acquired at every predetermined time, from a sample subject with the delirium or without delirium.

In this case, the delirium risk prediction model may be a model trained to predict the delirium risk based on all clinical data such as blood data, severity evaluation data, mental state evaluation data, bio signal data, medication data, and medical treatment data. However, data used for the training is not limited thereto and a combination of various clinical data may be used to train the prediction model.

In the meantime, when the delirium risk prediction model according to the present disclosure is trained, an evaluation to determine clinical data having a high relevance to prediction of the normal state which is not the delirium may be performed. In this case, the relevance evaluation may be performed based on a layer-wise relevance propagation (LRP) algorithm.

For example, clinical data having a high relevance to predict the delirium or clinical data having a high relevance to predict the normal state which is not the delirium may be determined by the LRP algorithm, from various clinical data such as initial blood data, severity evaluation data, mental state evaluation data, bio signal data, medication data, and medical treatment data.

As the clinical data having a high relevance is applied to the training of the prediction model as input data, the prediction model may be a model with an improved delirium prediction ability as compared with another model.

In the meantime, the delirium risk prediction model according to the present disclosure may be a prediction model based on a multi-layer perceptron (MLP) algorithm which is a multi-layer artificial neural network.

For example, the delirium risk prediction model of the present disclosure may be a multi-layered prediction model having an input layer to which blood data, severity evaluation data, mental state evaluation data, bio signal data, medication data, and medical treatment data are input, an output layer which predicts the delirium or a normal state which is not the delirium, and one hidden layer disposed between the input layer and the output layer.

More specifically, the delirium risk prediction model of the present disclosure may be configured to include one hidden layer configured by 64 nodes. Moreover, the prediction model may set a learning rate which may set a parameter for finding a weight which minimizes a prediction error during the delirium prediction learning to be 0.0009. Further, a momentum value which is a parameter value for increasing a learning speed while minimizing a prediction error may be set to 0.9. Further, the delirium risk prediction model of the present disclosure may be configured to use "rmsprop" as an optimization function which updates a parameter during the learning and use "relu" function as a function which determines a strength of transmitting an input value of various clinical data to an output value.

However, the type of delirium risk prediction model of the present disclosure is not limited thereto. For example, the prediction model may be a deep neural network (DNN), a convolutional neural network (CNN), a recurrent neural network (RNN), a deep convolutional neural network (DCNN), a restricted Boltzmann machine (RBM), a deep belief network (DBN), a single shot detector (SSD) model or a U-net based prediction model.

Hereinafter, a delirium risk predicting device according to an embodiment of the present disclosure and a delirium risk prediction system using the same will be described in more detail with reference to FIGS. 1A and 1B.

FIG. 1A illustrates a delirium risk prediction system based on a method and a device for predicting a delirium risk according to an embodiment of the present disclosure. FIG. 1B illustrates a configuration of a delirium risk predicting device according to an embodiment of the present disclosure.

Referring to FIG. 1A, a delirium risk prediction system 1000 according to an embodiment of the present disclosure is configured by a delirium risk prediction device 100, clinical data 300 including medical treatment data 310, medication data 320, bio signal data 330, blood data 340, severity evaluation data 350, and mental state evaluation data 360, acquired for an subject 200, a medical treatment 400, and a medical practitioner device 500.

In this case, the clinical data 300 may be first data which is measured or evaluated at an arbitrary timing, from the subject 200, but, it is not limited thereto.

More specifically, in the delirium risk prediction system 1000, the delirium risk predicting device 100 may be configured to receive various clinical data 300 which is initially measured or evaluated for the subject 200 and predict a mortality risk based on the clinical data.

In this case, the medical treatment 400 may be a bio signal measurement device which provides at least one bio signal data 330 from the group consisting of a body temperature, a pulse rate, an oxygen saturation, a systolic blood pressure, a diastolic blood pressure, a mean blood pressure, and a respiratory rate of the subject 200.

In the meantime, in the delirium risk prediction system 1000, the medical treatment data 310, the medication data 320, the blood data 340, the severity evaluation data 350, and the mental state evaluation data 360 may be acquired from an external system such as an electronic medical record (EMR) system.

Figure 1B:
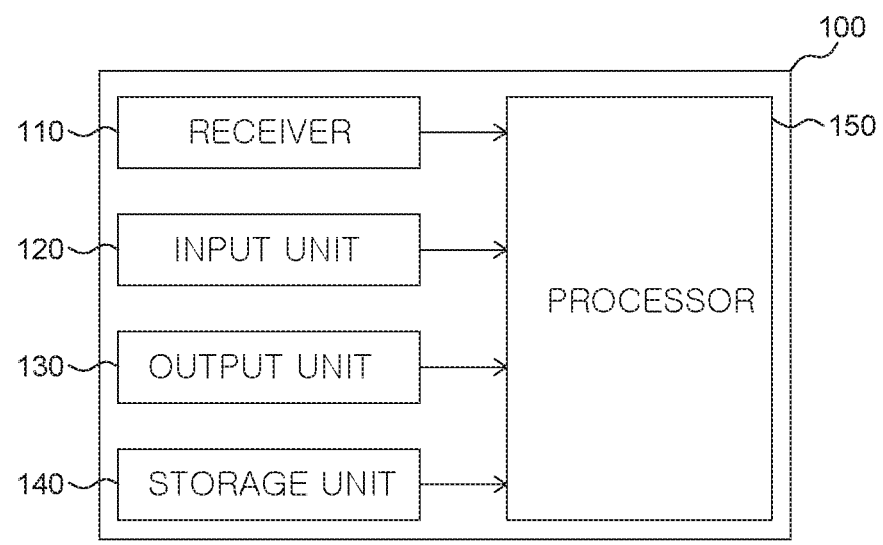
FIG. 1B illustrates a configuration of a delirium risk predicting device according to an embodiment of the present disclosure.

More specifically, referring to FIG. 1B, the delirium risk predicting device 100 includes a receiver 110, an input unit 120, an output unit 130, a storage unit 140, and a processor 150.

Specifically, the receiver 110 may be configured to receive clinical data 300 including the medical treatment data 310, the medication data 320, the bio signal data 330, the blood data 340, the severity evaluation data 350, and the mental state evaluation data 360 for the subject 200.

According to the characteristic of the present disclosure, the receiver 110 may be further configured to transmit a result predicted for the subject 200 determined by the processor to be described below to the medical practitioner device 500.

The input unit 120 may be a keyboard, a mouse, or a touch screen panel, but is not limited thereto. The input unit 120 may set the delirium risk predicting device 100 and instruct the operation of the delirium risk predicting device 100.

In the meantime, the output unit 130 may display various clinical data 300 received by the receiver 110. Moreover, the output unit 130 may display information associated with the diagnosis of the delirium predicted by the processor 150 on a display. Moreover, when the processor 150 determines that the delirium risk is high, the output unit 130 may be further configured to output a notification sound.

The storing unit 140 may be configured to store the various clinical data 300 for the subject 200 received by the receiver 110 and store the instruction of the delirium risk predicting device 100 set by the input unit 120. Moreover, the storage unit 140 is configured to store delirium prediction information of the subject 200 generated by the processor 150 to be described below. However, it is not limited to the above description and the storage unit 140 may store various information determined by the processor 150 to predict the delirium risk.

The processor 150 may be a component for providing a precise prediction result of the delirium risk predicting device 100. In this case, the processor 150 may operate based on a prediction model configured to predict the delirium risk based on various clinical data 300 for the purpose of precise delirium risk prediction.

In the meantime, the processor 150 may be configured to provide a notification to the medical practitioner device 500 when the subject 200 is predicted as a high risk group of the delirium by the delirium risk prediction model. Therefore, the medical practitioner may take a quick action for the subject 200.

Moreover, the processor 150 may be further configured to determine a delirium inducing drug based on the medication data 320 among various clinical data 300 and provide the delirium risk predicted for the subject 200 and the delirium inducing drug to the medical practitioner device 500.

Therefore, the medical practitioner may take a quick action for the subject 200.

As described above, since the delirium risk prediction system 1000 according to the present disclosure provides early diagnosis of delirium and early treatment of delirium for the subject 200, the delirium risk prediction system 1000 may be applied to various medical systems.

Figure 2:
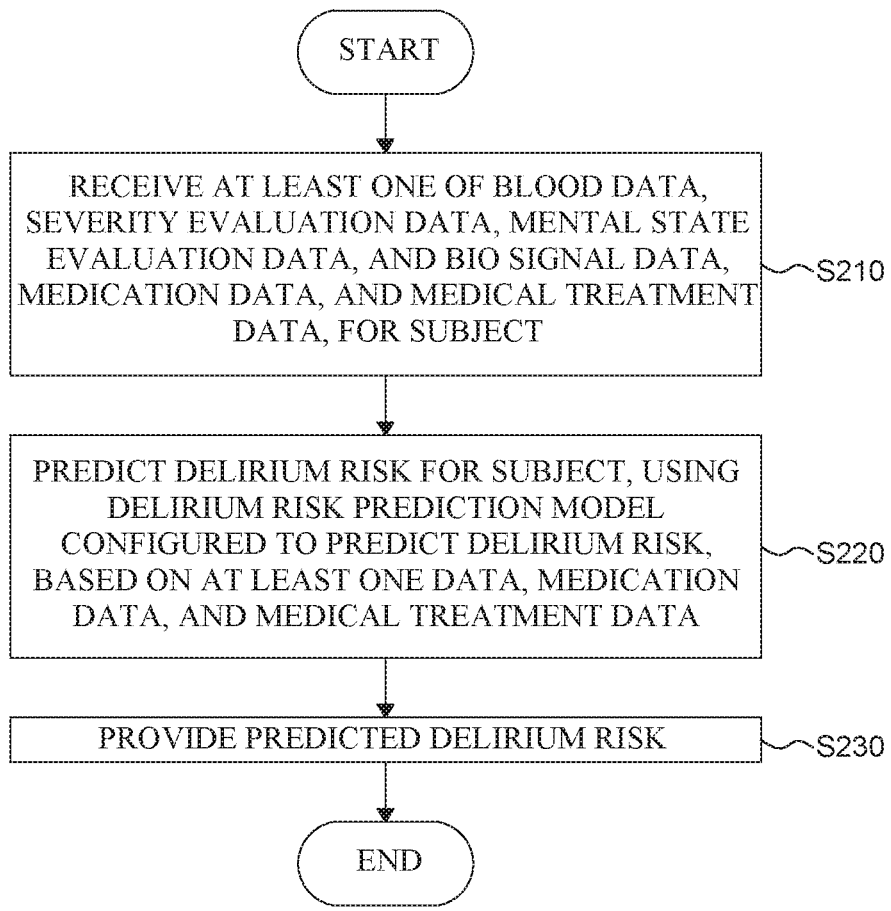
FIG. 2 illustrates a procedure of a delirium risk predicting method according to an embodiment of the present disclosure.

Hereinafter, a delirium risk predicting method according to an embodiment of the present disclosure will be described in detail with reference to FIG. 2. FIG. 2 illustrates a procedure of a delirium risk predicting method according to an embodiment of the present disclosure.

Referring to FIG. 2, the delirium risk predicting method according to the embodiment of the present disclosure receives at least one data of blood data, severity evaluation data, mental state evaluation data, and bio signal data, medication data, and medical treatment data from the subject in step S210 and predicts the delirium risk for the subject, using a delirium risk prediction model configured to predict the delirium risk based on at least one data, the medication data, and the medical treatment data in step S220. Finally, the method provides the delirium risk predicted for the subject in step S230.

More specifically, in the step S210 of receiving data, at least one data of the blood data, the severity evaluation data, the mental state evaluation data, and the bio signal data, and the medication data and the medical treatment data, which are initially measured or acquired for the subject, may be received.

According to the characteristic of the present disclosure, the medication data received in the step S210 of receiving data may be at least one of Ultracet, Midazolam, ultiva, ativan, pofol, fentanyl, precedex, IR codon, TARGIN 20/10, peridol, risperdal, zyprexa, seroquel, abilify, and pethidine.

For example, according to another characteristic of the present disclosure, the medical treatment data received in the step S210 of receiving data may be data indicating whether to perform at least one medical treatment of catheter, Foley, mechanical ventilator, restraint, and drainage.

According to another characteristic of the present disclosure, the blood data received in the step S210 of receiving data may be at least one value of blood urea nitrogen (BUN), pH, $HCO_3$, albumin (Alb), hemoglobin (Hb), hematocrit (Hct), bilirubin (BILI), Na, and neutrophil to lymphocyte ratio (NLR) measured from the blood separated from the subject.

According to another characteristic of the present disclosure, the severity evaluation data received in the step S210 of receiving data may be an acute physiology and chronic health evaluation (APACHE II) score.

According to another characteristic of the present disclosure, the mental state evaluation data received in the step S210 of receiving data may be a Richmond agitation and sedation scale (RASS) or state-trait anxiety inventory (STAI) score.

According to another characteristic of the present disclosure, the bio signal data received in the step S210 of receiving data may be a body temperature, a pulse rate, an oxygen saturation, a systolic blood pressure, a diastolic blood pressure, a mean blood pressure, and a respiratory rate for the subject measured from the bio signal metrology equipment. However, the bio signal data is not limited thereto and includes various measurement data associated with the health condition of the subject.

Next, in the step S220 of predicting the delirium risk, it is determined whether the subject is delirium or a normal state which is not the delirium, by the delirium risk prediction model configured to predict the delirium risk.

In this case, the delirium risk prediction model may be a model trained to predict the delirium risk based on clinical data such as initial blood data, severity evaluation data, mental state evaluation data, bio signal data, medication data, and medical treatment data received in the step S210 of receiving data.

For example, the delirium risk prediction model may be a model which receives learning data configured by at least one data of the blood data, the severity evaluation data, the mental state evaluation data, and the bio signal data, the medication data, and the medical treatment data for a delirium onset sample subject and a normal sample subject and is trained based on the learning data, by a step of predicting the delirium or the normal.

Moreover, the delirium risk prediction model may be a model which is configured to calculate a relevance score for the learning data to the delirium and predict the delirium risk, based on delirium related learning data determined by the step of determining delirium related learning data in a predetermined ranking, based on the relevance score.

Finally, in the step S230 of providing the delirium risk, information about the delirium diagnosis predicted in the above-described step S220 of predicting the delirium risk may be provided.

In the meantime, according to the characteristic of the present disclosure, a step of determining a delirium inducing drug based on medication data received in the step S210 of receiving data may be further performed.

Therefore, in the step S230 of providing the delirium risk, the delirium risk predicted for the subject and the delirium inducing drug may be provided.

According to another characteristic of the present disclosure, when the delirium risk for the subject is predicted by the delirium prediction model in the step S220 of predicting the delirium risk, in the step S230 of providing the delirium risk, a notification of the delirium risk for the subject is provided.

In the meantime, in the step S230 of providing the delirium risk, various information in addition to the above-described information may be provided. For example, in the step S230 of providing the delirium risk, additional information such as time information for the subject or caregiver's entrance, which may be effective to correct the delirium, may be further provided.

In accordance with the above-described procedure, the delirium risk predicting method according to the embodiment of the present disclosure may determine whether the delirium occurs in the subject in real time or predict the delirium risk before a predetermine time to provide information about the delirium risk, information about the delirium inducing drug, and an alarm notifying a high risk group. Therefore, the medical practitioner may early diagnose the delirium for the subject. Moreover, the medical practitioner may take a quick action for the high risk group of delirium.

Hereinafter, a delirium risk prediction model used for various embodiments of the present disclosure will be described in detail with reference to FIGS. 3A to 3D.

In this case, the delirium risk prediction model according to various embodiments of the present disclosure may be a model which is trained based on clinical data such as initial mental state evaluation data, bio signal data, medical treatment data, blood data, severity evaluation data, and medication data which are acquired once per day for two days in the 24 hours unit, from patients in the intensive care unit, configured by delirium patients or patients which are not delirium, but the learning method is not limited thereto. Moreover, the clinical data used to predict the delirium may be selected by various configurations depending on the learning method.

FIGS. 3A and 3B illustrate learning data of a delirium risk prediction model used for various embodiments of the present disclosure.

Referring to FIG. 3A, in order to train the delirium risk prediction model used for various embodiments of the present disclosure, 6386 data acquired from ICU of Gangnam Severance Hospital was used. More specifically, the training data is configured by 609 data for subjects determined as delirium during the entire ICU admission period and 2656 data for subjects whose delirium occurring date is missing or who has been determined not to be delirium at least once during the entire ICU admission period, among 6386 data.

Referring to FIG. 3B, the training data acquired from the samples of the delirium onset subjects and normal subjects is configured by the mental state evaluation data, the bio signal data, the medical treatment data, the blood data, the severity evaluation data, and the medication data.

More specifically, the mental state evaluation data for training may be configured by the RASS and STAI scores. The bio signal data for training may be configured by a pulse rate, a respiration rate, a body temperature, SBP, and DBP values. Moreover, the medical treatment data for training may be configured by whether to apply or perform catheter, Foley, mechanical ventilator, restraint, and drainage and whether to take nutrition. Further, the blood data for training may be configured by BUN—(blood urea nitrogen), pH-, HCO$_3$—, Alb—(albumin), Hb—(hemoglobin), Hct—(hematocrit), BILI—(Bilirubin), Na, and NLR (Neutrophil to Lymphocyte Ratio). Further, the severity evaluation data for training may be configured by APACHE scores. The medication data for training may be configured by Ultracet, Midazolam, ultiva, ativan, pofol, fentanyl, precedex, IR codon, TARGIN 20/10, peridol, risperdal, zyprexa, seroquel, abilify, pethidine, durogesic patch, morphine, and mypol.

In this case, the learning data may be initial data acquired once per day for two days in 24-hour unit from a patient. In this case, missing data for two days when the data is acquired may be processed as an average value or zero.

The delirium risk prediction model according to the present disclosure may be trained to determine whether the delirium occurs in the sample subject based on the learning data as described above.

Figure 3C:
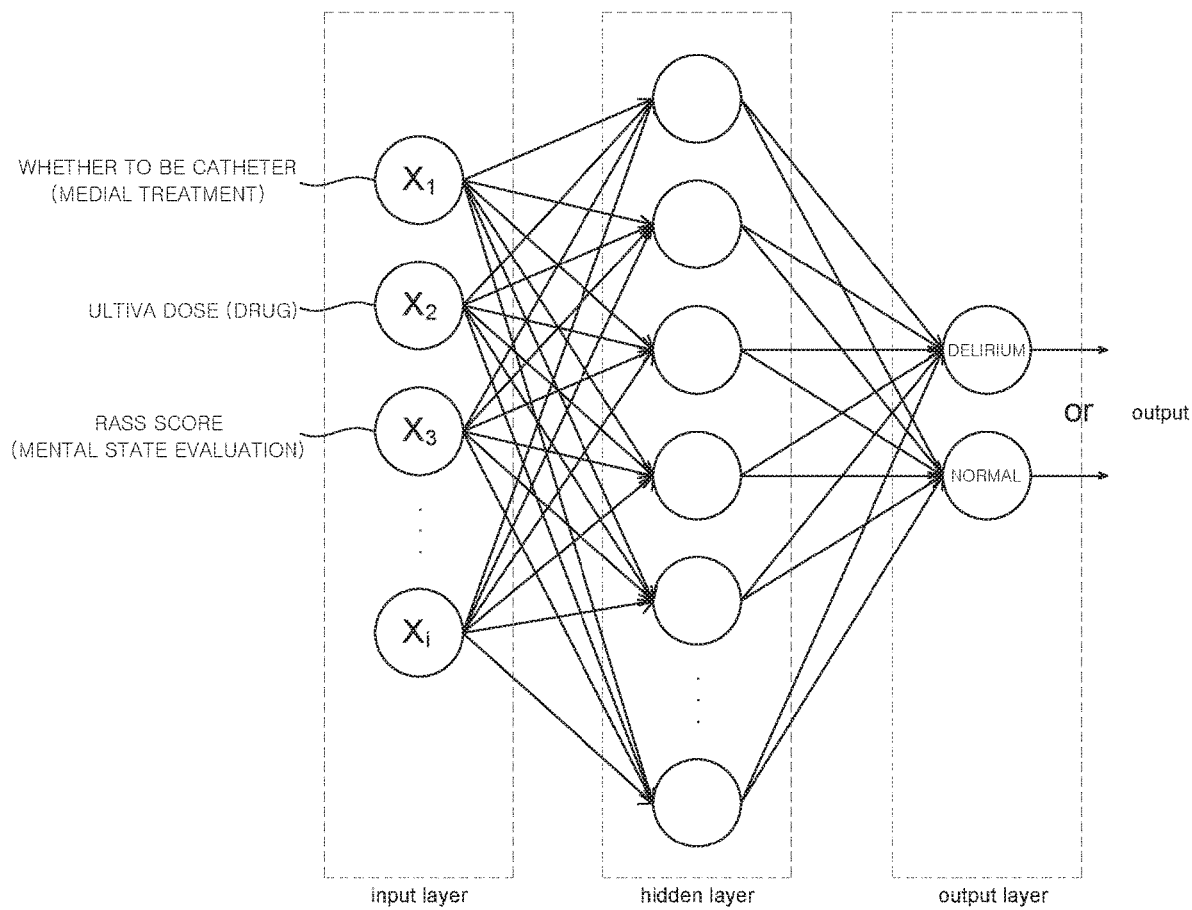
FIG. 3C illustrates a configuration of a delirium risk prediction model used for various embodiments of the present disclosure.

FIG. 3C illustrates a configuration of a delirium risk prediction model used for various embodiments of the present disclosure.

Referring to FIG. 3C, the delirium risk prediction model of the present disclosure may be a prediction model based on an MLP algorithm which is a multilayer artificial neural network.

More specifically, the delirium risk prediction model of the present disclosure may be a multi-layered prediction model having an input layer to which blood data, severity evaluation data, mental state evaluation data, bio signal data, medication data, and medical treatment data are input, an output layer which predicts the delirium or a normal state which is not the delirium, and one hidden layer disposed between the input layer and the output layer.

In this case, the delirium risk prediction model of the present disclosure may be configured to include one hidden layer configured by 64 nodes. Moreover, the prediction model may set a learning rate which may set a parameter for finding a weight which minimizes a prediction error during the delirium prediction learning to be 0.0009. Further, a momentum value which is a parameter value for increasing a learning speed while minimizing a prediction error may be set to 0.9. Further, the delirium risk prediction model of the present disclosure may be configured to use "rmsprop" as an optimization function which updates a parameter during the learning and use "relu" function as a function which determines a strength of transmitting an input value of various clinical data to an output value.

However, the type of delirium risk prediction model of the present disclosure is not limited thereto. For example, the prediction model may be a DNN, CNN, RNN, DCNN, RBM, DBN, or SSD model, or U-net based prediction model.

In the meantime, when the delirium risk prediction model according to the present disclosure is trained, an evaluation to determine clinical data having a high relevance to predict the normal state which is not the delirium may be performed. In this case, the relevance evaluation may be performed based on a layer-wise relevance propagation (LRP) algorithm.

Figure 3D:
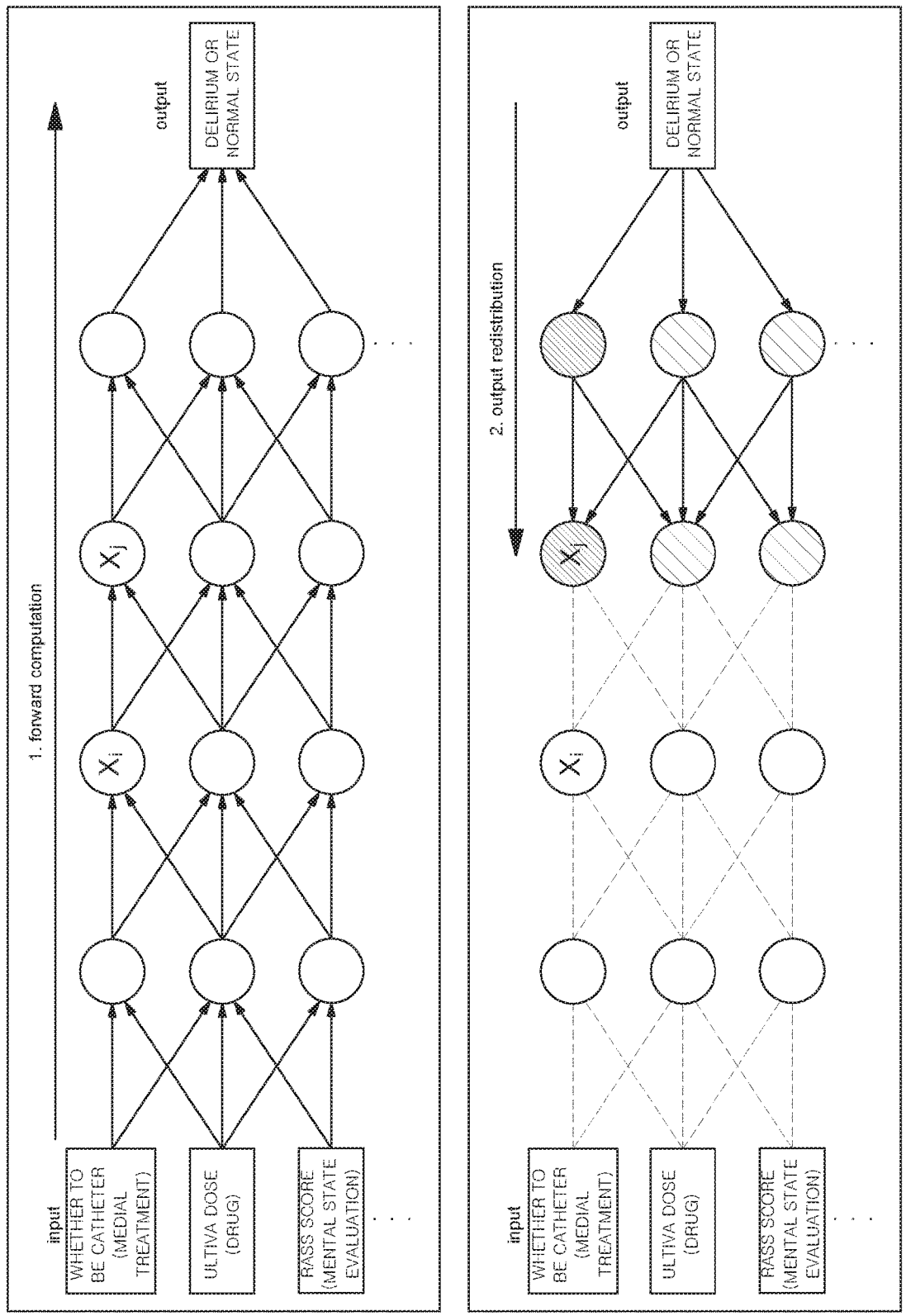
FIG. 3D illustrates an evaluation method of a delirium risk prediction model used for various embodiments of the present disclosure.

FIG. 3D illustrates an evaluation method of a delirium risk prediction model used for various embodiments of the present disclosure.

Referring to FIG. 3D, when a delirium prediction result is output by a delirium risk prediction model based on various clinical data, evaluation based on the LRP algorithm may be performed.

More specifically, according to this evaluation, a relevance of an input value of various clinical data such as clinical data of initial blood data, severity evaluation data, mental state evaluation data, bio signal data, medication data, and medical treatment data and an output value indicating to be delirium or normal state which is not delirium may be estimated.

More specifically, the relevance between the input value of various clinical data and the output value to be delirium or a normal state which is not delirium may be calculated by the following Equation 1.

$$r_i^{(L)} = \begin{cases} S_i(x) & \text{if the unit } i \text{ is the target unit of interest} \\ 0 & \text{otherwise} \end{cases}$$

$$r_i^{(l)} = \sum_j \frac{z_{ji}}{\sum_{i'} (z_{ji'} + b_j) + \epsilon \cdot \text{sign}\left(\sum_{i'} (z_{ji'} + b_j)\right)} r_j^{(l+1)}$$

Here, L refers to an output layer value, $Z_{ji}$ refers to a product of a weight of a l+1-st layer and a l-th layer and an input value of an l-th layer ($W_{ji}^{(l+1,1)}, x_i^{(l)}$). Moreover, $b_j$ may refer to a bias value of a j-th node.

Clinical data having a high relevance to predict the delirium or clinical data having a high relevance to predict a normal state which is not the delirium among the various clinical data may be determined by the calculated relevance score.

As the clinical data having a high relevance is applied to the training of the prediction model as input data, the delirium prediction ability of the prediction model of the present disclosure may be better than the other models.

In the meantime, the evaluation of the delirium risk prediction model may be performed based on various algorithms without being limited to the above-described LRP algorithm. For example, clinical data having a high relevance to predict the delirium or clinical data having a high relevance to predict the normal state which is not the delirium may be determined based on the randomized decision forest algorithm or penalized logistic regression algorithm.

Figure 4D:
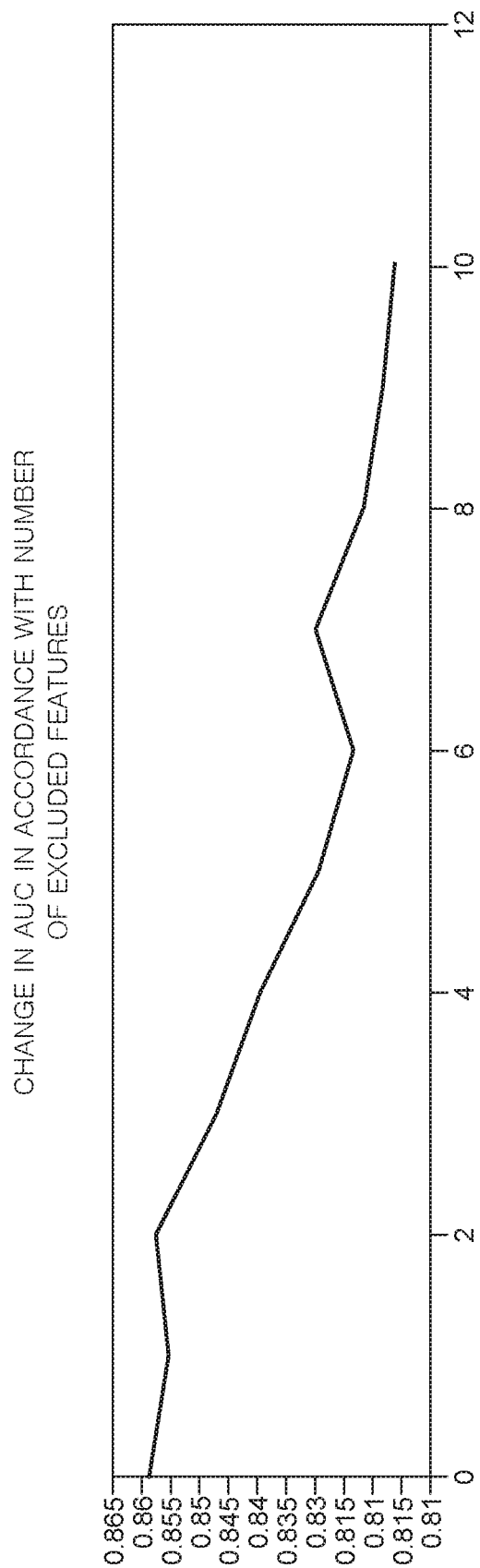
FIG. 4D illustrates performance change in accordance with change in clinical data in accordance with a relevance of delirium prediction for a delirium risk prediction model used for various embodiments of the present disclosure.

Example: Evaluation of Delirium Risk Prediction Model According to Various Embodiments of Present Disclosure Hereinafter, an evaluation result of a delirium risk prediction model used for various embodiments of the present disclosure will be described in detail with reference to FIGS. 4A to 4D. FIGS. 4A and 4B illustrate an evaluation result for a delirium risk prediction model used for various embodiments of the present disclosure. FIG. 4C illustrates clinical data in accordance with a relevance of delirium prediction for a delirium risk prediction model used for various embodiments of the present disclosure. FIG. 4D illustrates performance change in accordance with change in clinical data in accordance with a relevance of delirium prediction for a delirium risk prediction model used for various embodiments of the present disclosure.

Referring to FIG. 4A, an evaluation result of a delirium risk prediction model configured to predict delirium (positive) or normal state (negative) which is not delirium based on mental state evaluation data, bio signal data, medical treatment data, blood data, and severity evaluation data, excluding medication data from the above-described clinical data, is illustrated.

More specifically, referring to FIG. 4A (a), 609 data (487 for training and 122 for test) for subjects with delirium and 1019 data (487 for training and 532 for test) for normal subjects who are not delirium are used for training and evaluation of the prediction model.

Referring to FIG. 4A (b) and (c), a sensitivity for the prediction of the delirium of the prediction model is 0.8197, a specificity is 0.7387, and a precision is 0.7538, which are very high levels. Specifically, an ACU value which means a diagnosis ability is 0.8597 so that when the delirium risk prediction model trained by the learning data is applied to a delirium diagnosis system, the delirium risk for subjects may be predicted in advance with a high accuracy.

Referring to FIG. 4B, an evaluation result of a delirium risk prediction model configured to predict delirium (positive) or normal state (negative) which is not delirium based on medication data, mental state evaluation data, bio signal data, medical treatment data, blood data, and severity evaluation data is illustrated.

More specifically, referring to FIG. 4B (a), 609 data (122 for training and 487 for test) for subjects with delirium and 1019 data (532 for training and 487 for test) for normal subjects who are not delirium are used for training and evaluation of the prediction model.

Referring to FIG. 4B (b) and (c), a sensitivity for the prediction of the delirium of the prediction model is 0.8279, a specificity is 0.75, and a precision is 0.7645, which are very high levels. Specifically, it is understood that the sensitivity, the specificity, and the precision are improved from the evaluation result of the above-described prediction model excluding medication data of FIG. 4A.

In the meantime, the AUC value which indicates the diagnosis ability of the prediction model is 0.8585 so that the result is similar to the evaluation result of the above-described prediction model excluding the medication data of FIG. 4A.

According to the result, when the delirium risk prediction model which is used for various embodiments of the present disclosure is applied to the delirium diagnosis system, the delirium risk for subjects may be predicted with a high accuracy.

Referring to FIG. 4C, an influence (relevance) evaluation result of clinical data used for various embodiments of the present disclosure is illustrated. In this case, an average relevance calculated for each clinical data may refer to an influence to predict the delirium.

More specifically, referring to FIG. 4C (a), clinical data with a high relevance which has high influence to predict the delirium is illustrated. More specifically, the average relevance of feature data indicating whether to perform second-day catheter treatment (medical treatment data) is 0.523812, which is higher than that of the other clinical data.

That is, in order to predict the delirium, the influence of data indicating whether to perform catheter treatment acquired on the second day is high.

Moreover, it shows that medical treatment data indicating whether to perform second day Foley treatment, whether to perform second day restraint treatment, whether to perform first day restraint treatment, whether to perform first day Foley treatment, and whether to perform second day mechanical ventilator treatment has a higher average relevance in this order. Next, it shows that the average relevance of medication data is high.

This result means that when the delirium is predicted based on the initial data, the medical treatment data and the medication data among various clinical data provide high influence to predict the delirium. That is, when the medical treatment data and the medication data are used, it is possible to predict the delirium for subjects with excellent diagnosis ability.

Referring to FIG. 4C (b), clinical data having a high influence to predict a normal state which is not delirium is illustrated. More specifically, the average relevance of feature data indicating whether to perform first-day catheter treatment (medical treatment data) is −0.39132, which is the lowest.

That is, in order to predict the normal state which is not the delirium, the influence of whether to perform catheter treatment acquired on the first day may be high. In other words, the data to predict the delirium may have the lowest relevance.

Moreover, the average relevance is lower in the order of a second day RASS score, whether to perform first day drainage treatment, and whether to first day mechanical ventilator treatment.

In the meantime, referring to FIG. 4D, an AUC value obtained by sequentially accumulating and excluding upper 10 clinical data having high average relevance (whether to perform second day catheter treatment, whether to perform second day Foley treatment, whether to perform second day restraint treatment, whether to perform first day restraint treatment, whether to perform first day Foley treatment, whether to perform second day mechanical ventilator treatment, a first day ultiva dose, a second day ultracet dose, a first day morphine dose, and a first day mypol dose) in FIG. 4C (a) is illustrated.

More specifically, the AUC value for delirium prediction is reduced by excluding clinical data having a high average relevance, that is, a high influence to predict the delirium.

This means that the performance of predicting the delirium is lowered by excluding the clinical data having a high influence.

Therefore, the delirium risk prediction model used for various embodiments of the present disclosure may be configured to use clinical data having a high average relevance as learning data. Therefore, the delirium risk prediction model may provide a delirium prediction result with an improved diagnosis ability than the other prediction model, to predict the delirium.

According to the result of the above-described embodiment, it is confirmed that the delirium risk prediction model used for various embodiments of the present disclosure predicts the delirium risk with a high accuracy. Moreover, it is confirmed that the prediction model of the present disclosure has an excellent diagnosis ability in accordance with the result having a high AUC value.

Therefore, according to the present disclosure, a good prognosis for treatment may be provided by advancing a treatment timing for the delirium.

Specifically, the present disclosure can provide a delirium risk prediction system based on clinical data such as bio signal data, blood data, mental state evaluation and severity evaluation data as well as initial medication data and medical treatment data acquired from the subjects, thereby providing early diagnosis of the delirium for the subject.

Therefore, the present disclosure may provide effects such as increased survival rate of the delirium onset subject, prevention of complications, and reduced treatment costs.

Moreover, according to the present disclosure, when there is delirium inducing drug in the received medication data, a feedback for providing the information is provided so that medical practitioners may take a quick action for the delirium such as discontinuation of administration of delirium inducing drugs.

Further, according to the present disclosure, when the delirium is predicted for the subject by the prediction model, an alarm is provided to notify the delirium risk so that caregivers or medical practitioners may easily recognize a high risk group of delirium for subjects who are required to be consistently monitored, such as critically ill patients.

Although the exemplary embodiments of the present disclosure have been described in detail with reference to the accompanying drawings, the present disclosure is not limited thereto and may be embodied in many different forms without departing from the technical concept of the present disclosure. Therefore, the exemplary embodiments of the present disclosure are provided for illustrative purposes only but not intended to limit the technical concept of the present disclosure. The scope of the technical concept of the present disclosure is not limited thereto. Therefore, it should be understood that the above-described exemplary embodiments are illustrative in all aspects and do not limit the present disclosure. The protective scope of the present disclosure should be construed based on the following claims, and all the technical concepts in the equivalent scope thereof should be construed as falling within the scope of the present disclosure.

What is claimed is:

1. A delirium risk predicting method implemented by a processor, the method comprising:

receiving blood data, severity evaluation data, mental state evaluation data, and bio signal data, medication data, and medical treatment data, for a subject, wherein the blood data is taken from a blood sample separated from the subject and includes one of blood urea nitrogen, pH, HCO3, albumin (Alb), hemoglobin, hematocrit (Hct), Bilirubin (BILI), Na, and neutrophil to lymphocyte ratio (NLR);

predicting a delirium risk for the subject, using a delirium risk prediction model configured to predict a delirium risk, based on the blood data, the severity evaluation data, the mental state evaluation data, the bio signal data, the medication data, and the medical treatment data; and providing the delirium risk predicted for the subject, wherein the blood data, the medication data, and the medical treatment data are defined as initial data which is evaluated or measured only once for the subject, wherein the delirium risk prediction model is a model trained by receiving learning data configured by at least one of blood data, severity evaluation data, mental state evaluation data, and bio signal data, medication data, and medical treatment data for a delirium sample subject and a normal sample subject;

calculating a relevance score to the delirium for the learning data; and determining delirium related learning data within a predetermined ranking, based on the relevance score and predicting to be delirium or normal based on delirium related learning data, wherein the relevance score is defined as a relevance between an input value and an output value indicating to be delirium or normal state.

2. The delirium risk predicting method according to claim 1, wherein the mental state evaluation data is a Richmond agitation and sedation scale (RASS) or state-trait anxiety inventory (STAI) score.

3. The delirium risk predicting method according to claim 1, wherein the severity evaluation data includes acute physiology and chronic health evaluation (APACHE II) score.

4. The delirium risk predicting method according to claim 1, wherein the bio signal data includes at least one of a pulse rate, a respiration rate, a body temperature, a systolic blood pressure (SBP), and a diastolic blood pressure (DBP).

5. The delirium risk predicting method according to claim 1, wherein the medication data includes at least one of Ultracet™, Midazolam™, Ultiva™, Ativan™, Pofol™, fentanyl, Precedex™, IR codon™, TARGIN 20/10™, Peridol™, Risperdal™, Zyprexa™, Seroquel™, Abilify™, pethidine, Durogesic patch™, morphine, and Mypol™.

6. The delirium risk predicting method according to claim 1, wherein the medical treatment data includes at least one medical treatment data of catheter, Foley, mechanical ventilator, restraint, and drainage.

7. The delirium risk predicting method according to claim 1, wherein the initial data is defined as initial data which is initially evaluated or measured for the subject in a predetermined time unit for a hospitalization period.

8. The delirium risk predicting method according to claim 1, further comprising:
determining a delirium inducing drug based on the medication data,
wherein the providing of the delirium risk includes:
providing the delirium risk predicted for the subject and the delirium inducing drug.

9. The delirium risk predicting method according to claim 1, wherein the providing of the delirium risk includes providing a notification of a delirium risk for the subject when the delirium risk for the subject is predicted by the delirium risk prediction model.

10. The delirium risk predicting method according to claim 1, wherein the calculating a relevance score to the delirium includes:
calculating a relevance score to the delirium for the learning data, using a layer-wise relevance propagation (LRP) algorithm and
wherein determining delirium related learning data includes:
determining delirium related learning data within a predetermined ranking, based on the relevance score.

11. A delirium risk predicting method implemented by a processor, the method comprising:
receiving blood data, severity evaluation data, mental state evaluation data, bio signal data, medication data, and medical treatment data, for a subject, wherein the blood data is taken from a blood sample separated from the subject and includes one of blood urea nitrogen, pH, HCO3, albumin (Alb), hemoglobin, hematocrit (Hct), Bilirubin (BILI), Na, and neutrophil to lymphocyte ratio (NLR);
predicting a delirium risk for the subject, using a delirium risk prediction model configured to predict a delirium risk, based on the blood data, the severity evaluation data, the mental state evaluation data, the bio signal data, the medication data, and the medical treatment data; and
providing the delirium risk predicted for the subject,
wherein the blood data, the medication data, and the medical treatment data are defined as initial data which is evaluated or measured only once for the subject, and,
wherein the delirium risk prediction model is a multilayer perceptron (MLP) algorithm based prediction model, and a model trained by receiving learning data configured by at least one of blood data, severity evaluation data, mental state evaluation data, bio signal data, medication data, and medical treatment data for a delirium sample subject and a normal sample subject;
calculating a relevance score to the delirium for the learning data; and
determining delirium related learning data within a predetermined ranking, based on the relevance score and predicting to be delirium or normal based on the delirium related learning data,
wherein the relevance score is defined as a relevance between an input value and an output value indicating to be delirium or normal state.

12. A delirium risk predicting device implemented by a processor, the device comprising:
a receiver configured to receive blood data, severity evaluation data, mental state evaluation data, bio signal data, medication data, and medical treatment data, for a subject, wherein the blood data is taken from a blood sample separated from the subject and includes one of blood urea nitrogen, pH, HCO3, albumin (Alb), hemoglobin, hematocrit (Hct), Bilirubin (BILI), Na, and neutrophil to lymphocyte ratio (NLR); and
a processor configured to communicate with the receiver,
wherein the processor is further configured to predict a delirium risk for the subject, using a delirium risk prediction model configured to predict a delirium risk, based on the blood data, the severity evaluation data, the mental state evaluation data, the bio signal data, the medication data, and the medical treatment data and provide the delirium risk predicted for the subject, and the blood data, the medication data, and the medical treatment data are defined as initial data which is evaluated or measured only once for the subject,
wherein the delirium risk prediction model is a model trained by receiving learning data configured by at least one of blood data, severity evaluation data, mental state evaluation data, and bio signal data, medication data, and medical treatment data for a delirium sample subject and a normal sample subject;
wherein the processor is further configured to calculate a relevance score to the delirium for the learning data and to determine delirium related learning data within a predetermined ranking, based on the relevance score and predicting to be delirium or normal based on delirium related learning data,
wherein the relevance score is defined as a relevance between an input value and an output value indicating to be delirium or normal state.

13. The delirium risk predicting device according to claim 12, wherein the initial data is defined as initial data which is initially evaluated or measured for the subject in a predetermined time unit for a hospitalization period.

14. The delirium risk predicting device according to claim 12, wherein the processor is further configured to determine a delirium inducing drug based on the medication data and provide the delirium risk predicted for the subject and the delirium inducing drug.

15. The delirium risk predicting device according to claim 12, wherein the processor is further configured to provide a notification of a delirium risk for the subject when the delirium risk for the subject is predicted by the delirium risk prediction model.

16. The delirium risk predicting device according to claim 12, wherein the medication data includes at least one of Ultracet™, Midazolam™, Ultiva™, Ativan™, Pofol™, fentanyl, Precedex™, IR codon™, TARGIN 20/10™, Peridol™, Risperdal™, Zyprexa™, Seroquel™, Abilify™, pethidine, Durogesic patch™, morphine, and Mypol™.

17. The delirium risk predicting device according to claim 12, wherein the medical treatment data includes at least one medical treatment data of catheter, Foley, mechanical ventilator, restraint, and drainage.

* * * * *